| United States Patent [19] | [11] Patent Number: 4,895,852 |
| Higa et al. | [45] Date of Patent: * Jan. 23, 1990 |

[54] ANTITUMOR ALKALOIDS

[75] Inventors: Tatsuo Higa, Okinawa, Japan; Ryuichi Sakai, Champaign, Ill.; Toshio Ichiba, Nagasaki, Japan

[73] Assignee: Harbor Branch Oceanographic Institution, Inc., Ft. Pierce, Fla.

[*] Notice: The portion of the term of this patent subsequent to Jan. 23, 2007 has been disclaimed.

[21] Appl. No.: 124,672

[22] Filed: Nov. 24, 1987

[51] Int. Cl.$^4$ .................. A61K 31/475; C07D 519/00
[52] U.S. Cl. ..................................... 514/281; 540/478
[58] Field of Search ......................... 540/478; 514/281

[56] References Cited

U.S. PATENT DOCUMENTS 4,631,149 12/1986 Rinehart, Jr. et al. ............. 540/546

OTHER PUBLICATIONS

Rinehart, Jr. et al., J. Am. Chem. Soc., vol. 106, No. 5, pp. 1524-1526, (1984).
Kobayashi et al., J. Am. Chem. Soc., vol. 106, No. 5, pp. 1526-1528, (1984).
Uemura et al., J. Am. Chem. Soc., vol. 107, No. 16, pp. 4796-4798, (1985).
Sakai et al., J. Am. Chem. Soc., vol. 108, No. 20, pp. 6404-6405, (10/01/86).
Nakamura et al., Tetrahedron Letters, vol. 28, No. 6, pp. 621-624, (02/87).
Baslow et al., Chemical Abstracts, vol. 73:64847w, (1970).
Bossier et al., Chemical Abstracts, vol. 75:72510n, (1971).
Stempien et al., Chemical Abstracts, vol. 86:95905m, (1977).
Ballantine et al., Chemical Abstracts, vol. 87:152455m, (1977).
Targett et al., Chemical Abstracts, vol. 102:76154v, (1985).
Seldes et al., Chemical Abstracts, vol. 103:120351g, (1985).
Findlay et al., Chemical Abstracts, vol. 103:211558w, (1985).
Mebs et al., Chemical Abstracts, vol. 104:63871w, (1986).

*Primary Examiner*—Mukund J. Shah
*Assistant Examiner*—Diana G. Rivers
*Attorney, Agent, or Firm*—Carroll F. Palmer

[57] ABSTRACT

This invention relates to antitumor alkaloid compositions, a process of producing the compositions and a method for inhibiting tumors utilizing the compositions. More particularly, the compositions are antitumor alkaloids which are derived from marine organisms, i.e., the marine sponge Xestospongia, sp.

8 Claims, No Drawings

ANTITUMOR ALKALOIDS

FIELD OF THE INVENTION

This invention relates to new cyclic organic compounds which have useful antitumor activity. More particularly, this invention relates to new cyclic alkaloid antitumor compositions derived from marine organisms, i.e., marine sponge, *Xestospongia* sp. and their methods of use.

BACKGROUND OF THE INVENTION

Various tumor related diseases inflict man. Considerable research has been devoted to oncology and antitumor measures. Tumors are common in a variety of mammals and the prevention, control of the growth and regression of tumors in mammals is important to man. The term tumor refers to abnormal masses of new tissue growth which is discordant with the economy of the tissue of orgin or of the host's body as a whole.

Tumors inflict mammals and man with a variety of disorders and conditions including various forms of cancer and resultant cancerous cachexia. Cancerous cachexia refers to the symptomatic discomfort that accompanies the infliction of a mammal with a tumor. These symptoms include weakened condition of the inflicted mammal as evidenced by, for example, weight loss. The seriousness of cancer is well known, e.g., cancer is second only to heart and vascular diseases as a cause of death in man.

Considerable research and resources have been devoted to oncology and antitumor measures including chemotherapy. While certain methods and chemical compositions have been developed which aid in inhibiting, remitting or controlling the growth of tumors new methods and antitumor chemical compositions are needed.

Marine organisms and particularly marine sponges are a potential source for chemically and biologically interesting molecules of great diversity. Some such molecules derived from sponges are described in Scheuer, P. J. Ed., *Marine Natural Products, Chemical and Biological Perspectives*; Academic Press; N.Y., 1978-1983; Vol. I-V; Faulkner, D. J. *Natural Products Reports* 1984, 551-598; Uemura, D.; Takahashi, K.; Yamamoto, T.; Katayama, C.; Tanaka, J.; Okumura, Y.; Hirata, Y. *J. Am. Chem. Soc.* 1985, 107, 4796-4798. The entire disclosures of these references are hereby incorporated herein by reference.

Other interesting compositions derived from marine organisms (i.e., caribbean tunicate) and containing a β-Carboline system are described by K. L. Rinehart, Jr., J. Kobayashi, G. C. Harbour, R. G. Hughes, Jr., S. A. Mizsak, T. A. Scahill, in *J. Am. Chem. Soc.*, 106, 1524 (1984); J. Kobayashi, G. C. Harbour, J. Gilmore and K. L. Rinehart, Jr., ibid., at 1526. Also of interest are compositions disclosed by R. Sakai, T. Higa, C. W. Jefford, and G. Bernardinelli, in *J. Am. Chem. Soc.*, 108, 6404 (1986) and by H. Nakamura, S. Deng, J. Kobayaski, Y. Ohizumi, Y. Tomotake, T. Matsuzaki, and Y. Hirata, in *Tetrahedron Lett.*, 28, 621 (1987).

Certain cyclic alkaloid compositions, e.g., manzamines A-D derived from extracts of the marine sponge Haliclona sp., have been found to possess useful antitumor activity. Co-pending applications of Higa et al., U.S. Ser. No. 879,094 filed June 26, 1986 and U.S. Ser. No. 943,609 filed Dec. 18, 1986 are directed to antitumor alkaloid compositions including manzamines A-D:

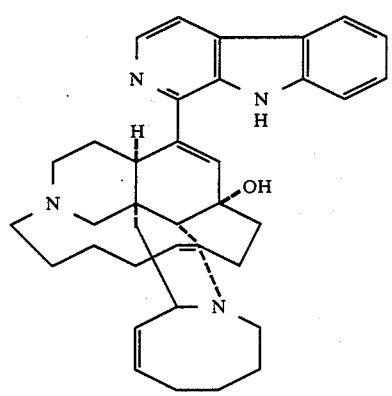

A

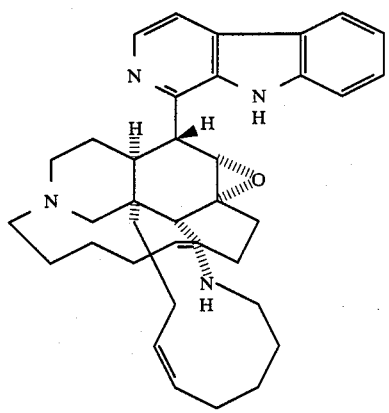

B

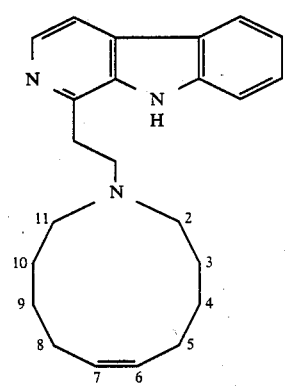

C

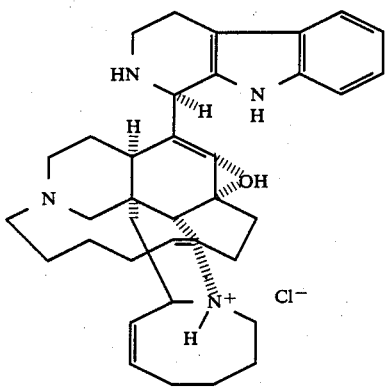

the entire disclosures of these co-pending applications are hereby incorporated herein by reference. The present invention is also directed to useful antitumor alkaloid compositions which are derived from the marine sponge *Xestospongia* sp.

SUMMARY OF THE INVENTION

It is therefore an object of the invention to provide novel compositions which are useful as antitumor agents and a process for producing such novel antitumor compositions.

Additional objects and advantages of the invention will be set forth, in part, in the description which follows and in part will be obvious from this description, or may be learned by the practice of the invention. The objects and advantages of the invention are realized and obtained by means of the compositions, processes, methods, and the combinations particularly pointed out in the appended claims.

To achieve the objects in accordance with the purposes of the invention, as embodied and fully described herein, the invention comprises a composition of one of formula (I):

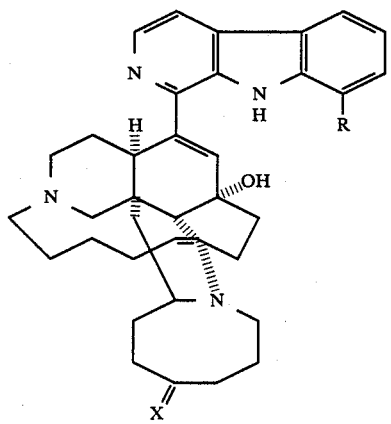

wherein R is a hydrogen, halogen, hydroxy, or lower acyloxy group; and X is a double bonded oxygen, or is the same or different and is any two of a hydrogen, hydroxy, lower alkyl, lower alkoxy, or lower acyloxy group wherein said lower alkyl, alkoxy, or acyloxy groups have preferably, from 1 to 5 carbon atoms.

Other embodiments of the invention include compositions according to Formula I wherein the double bonds are partially or fully reduced.

In further embodiments of the invention the composition is a mineral or organic acid salt of compositions according to Formula I or of compositions according to Formula I wherein at least one double bond is reduced.

In preferred embodiments of the invention, the composition is substantially pure. In further preferred embodiments of the invention R is a hydrogen or hydroxy group and X is an oxygen.

In more preferred embodiments of the invention, the invention comprises a composition of one of the following formulae, which are designated herein as manzamine E and F:

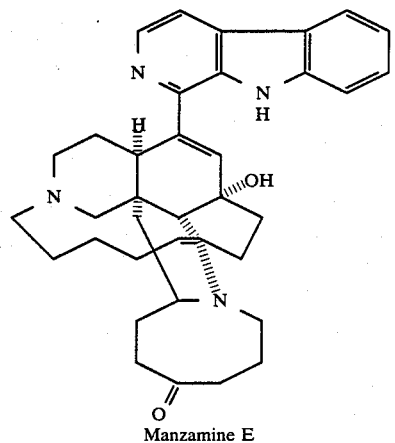

Manzamine E

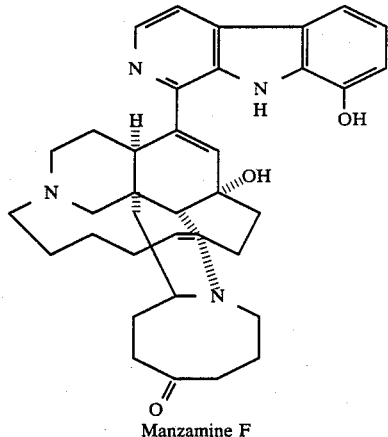

Manzamine F

As embodied and fully described herein, the invention also comprises an antitumor composition comprising, as active ingredient, an effective antitumor amount of one or more compounds according to Formula I; a compound according to Formula I wherein at least one double bond is reduced; an acid salt of a compound according to Formula I or an acid salt of a compound according to Formula I wherein at least one double bond is reduced; and a non-toxic pharmaceutically acceptable carrier or diluent.

In preferred embodiments the active ingredient of the antitumor composition comprises an effective amount of manzamine E or F.

As embodied and fully described herein, the invention also comprises a process to produce the compounds of Formula I and their reduced or acid salt derivatives and preferably, manzamines E and F. The process comprises the steps of collecting marine sponge *Xestospongia*, sp.; contacting the sponge with at least one suitable organic solvent; concentrating the extract to an aqueous suspension; extracting the aqueous suspension with at least one suitable organic solvent to obtain an organic extract comprising a compound according to Formula I or their reduced or acid salt derivatives; and isolating a compound according to Formula I or said acid salt or reduced derivatives of Formula I from the extract.

In preferred embodiments of the invention the suitable organic solvent is selected from the group consisting of acetone, methyl ethyl ketone, ethyl acetate, methanol, ethanol, methyl isobutyl ketone, and mixtures thereof.

As embodied and fully described herein, the invention further comprises a method for inhibiting tumors in a host and a therapeutic method for treating cancerous cachexia comprising contacting a tumor with an effective antitumor amount of one or more compounds of Formula I or their reduced or acid salt derivatives, or manzamine E or F.

It is to be understood that both the foregoing general and the following detailed description are exemplary and explanatory only and are not intended to be restrictive of the invention as claimed.

DETAILED DESCRIPTION OF THE PREFERRED EMBODIMENTS OF THE INVENTION

Reference will now be made in detail to present preferred embodiments of the invention, examples of which are illustrated in the following example section.

In accordance with the invention novel compositions are provided to achieve the objects in accordance with the purposes of the invention, as embodied and fully described herein, the invention comprises compounds of the formula (I):

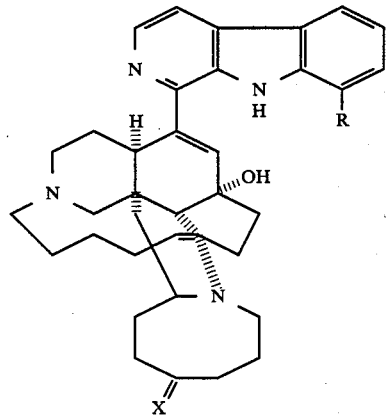

R is a hydrogen, halogen, hydroxy, or lower acyloxy group; and X is a double bonded oxygen or is the same or different and is any two of a hydrogen, hydroxy, lower alkyl, lower alkoxy, or lower acyloxy group, wherein said lower alkyl, alkoxy or acyloxy groups have from 1 to 5 carbon atoms.

In other embodiments of the invention the double bonds in the compound Formula I are partially or fully reduced.

In further embodiments of the invention the composition is a mineral acid (e.g. HCl, $H_2SO_4$, $H_3PO_4$, $HNO_3$, etc.) or organic acid salt of compounds according to Formula I or of compounds according to Formula I wherein at least one double bond is reduced.

In more preferred embodiments of the invention, the invention comprises compositions designated as manzamine E and F of the formulae:

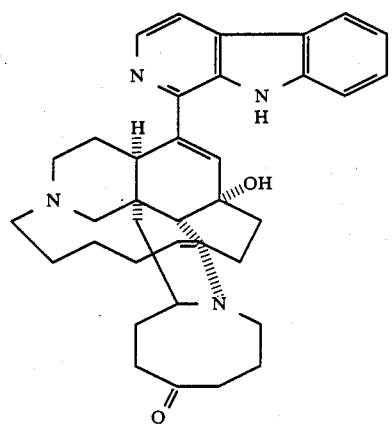

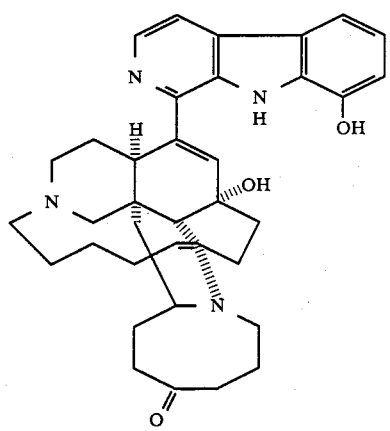

In accordance with the invention, an antitumor composition is provided comprising as active ingredient an effective antitumor amount of one or more of the compounds described above and identified by Formula I and their reduced or acid derivatives, or manzamine E or F; and a non-toxic pharmaceutically acceptable carrier or diluent. While effective amounts may vary, as conditions in which the antitumor compositions are used vary, a minimal dosage required for activity is generally between 0.01 and 100 micrograms against $10^5$ tumor cells. The compositions of the invention are indicated to be active for inhibiting a diverse range of tumors and tumor cells as demonostrated by, but not limited to, p-388 murine leukemia cells, and including human lung, colon and mammary tumors such as lung carcinoma A549, ileocecal adenocarcinoma HCT-8, human breast cancer cells MDAMB and other animal tumor and leukemia cells. Useful examples of non-toxic pharmaceutically acceptable carriers or diluents include, but are not limited to, the following: ethanol, dimethyl sulfoxide and glycerol.

In accordance with the invention, a method for inhibiting tumors in a host is provided comprising contacting a tumor with an antitumor amount of one or more compounds according to Formula I and their reduced or acid derivatives, or manzamine E or F. The effectiveness of the compositions of the invention for inhibiting tumors and tumor cells indicates their usefulness for controlling tumors in hosts including mammals and for treating cancerous cachexia.

In accordance with the invention, a process to produce compounds according to Formula I and their reduced or acid salt derivatives, or manzamine E and F is provided comprising the steps of: collecting marine sponge *Xestospongia* sp.; contacting the sponge with at least one suitable organic solvent to obtain an organic extract comprising a composition according to Formula I or their reduced or acid salt derivatives, or manzamine E or F; and isolating a compound according to Formula I or their reduced or acid salt derivative, or manzamine E or F therefrom.

A detailed description and explanation of a preferred embodiment of the process of the invention to produce the compounds according to Formula I and their reduced or acid salt derivatives, or manzamine E or F is as follows;

The marine sponge *Xestospongia* sp. is collected by SCUBA off Miyako Island, Okinawa. The sponge is brown-orange alive and tan preserved in ethanol. It is thickly encrusting to massive, with erect tubes. The sponge is compressible and easily torn, but not fragile, and its surface is smooth.

Identification of the sponge to the family Petrosiidae and genus *Xestospongia* is based on microscopic examination of taxonomic voucher specimens, one of which has been deposited with the Indian River Coastal Zone Museum (Catalog No. 003:00035) located at the Harbor Branch Oceanographic Institution, Inc, Ft. Pierce, Fla.

Both the ectosomal and choanosomal skeletons are isotropic reticulations of multispicular tracts. The spicules are exclusively strongyles in one size category, ranging in size from 90–130 $\mu$m in length by 5 $\mu$m in diameter. The marine sponge is contacted with and steeped in methanol and then acetone as first solvent for about 10 to 48 hours to obtain an extract which is concentrated to yield an aqueous suspension (the water is derived from the natural water content of the sponge). This step may be repeated to thoroughly extract the sponge and the additional aqueous suspensions may be combined. The aqueous suspension is then extracted with ethyl acetate as a second solvent to obtain an extract which comprises a compound according to Formula I or their reduced or acid salt derivatives, or manzamine E or F. The ethyl acetate extract is concentrated to give a brown oil which is separated by chromatography using silica gel with chloroform-heptane-2-propanol-aqueous ammonia (25:5:1:1) and then with chloroform-methanol (20:1) as eluents. A fraction eluted with the latter solvent system was further fractionated using a Lobar Si-60 column with chloroform-methanol (25:1) and then purified by HPLC (silica gel, chloroform-methanol 30:1) to give the compounds of the invention.

While methanol and acetone are the presently preferred choices for the first and second extracting solvents and ethyl acetate is the preferred second solvent, other suitable solvents may be substituted. A suitable solvent should be capable of extracting a compound according to any one of Formula I or their reduced or acid salt derivative or manzamine E or F from other components of the marine sponge. Suitable first and second solvents which may be substituted for methanol, acetone or ethyl acetate include, but are not limited to, the following organic solvents: methyl ethyl ketone; acetone; methanol; ethanol; methyl isobutyl ketone; methylene chloride; chloroform; ether; and tetrahydrofuran.

Any suitable fractionation and isolation techniques may be utilized to isolate and purify the compounds of the invention prepared in accordance with the processes of the invention. Suitable fractionation techniques include various chromotography techniques such as, high pressure liquid chromatography (HPLC), and with suitable columns as would be known to those skilled in the art including silica gel, Sephadex LH-20; ammonia-treated silica gel; RP-18, RP-8, and Li-Chrosorb $NH_2$ column. These columns are eluted with suitable eluents such as: heptane; ethyl acetate; methylene chloride; methanol; isopropyl alcohol; and various combinations and ratios thereof as would be known to those skilled in the art. Countercurrent chromatography techniques may also be useful for isolating compositions of the invention.

EXAMPLES

The invention will now be illustrated by examples. The examples are not intended to be limiting of the scope of the present invention. In conjunction with the detailed and general description above, the examples provide further understanding of the present invention and outline a process for producing compositions of the invention.

The following examples represent preferred embodiments of the compositions, processes and methods of the invention for satisfying the stated objects of the invention. The starting materials and reagents in the examples whose method of preparation are not indicated are commercially available from sources known to the art such as chemical supply houses.

EXAMPLES 1 and 2

The antitumor cyclic alkaloids of the invention were prepared from a marine sponge, *Xestospongia* sp., according to the following procedures.

Example 1 and 2
Preparation of Manzamine E and F

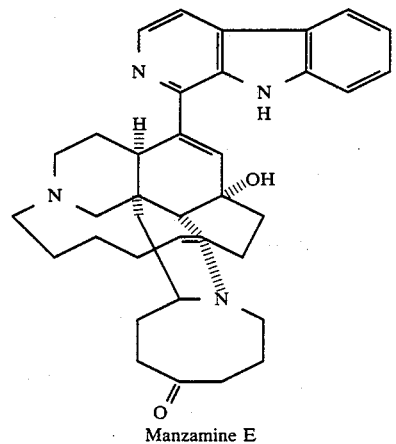

Manzamine E

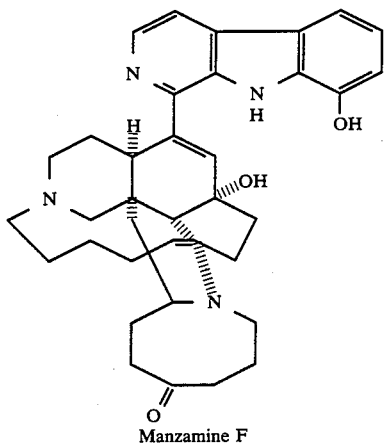

Manzamine F

A sample (6 kg) of a sponge, *Xestospongia* sp., was collected near Miyako Island, Okinawa. The sample was extracted by steeping in methanol (5 L.) and then in acetone (5 L.). The extracts were combined and concentrated to give an aqueous suspension which was separted by chromatography using silica gel with chloroform-heptane-2-propanol-aqueous ammonia (25:5:1:1) and then with chloroform-methanol (20:1). A fraction eluted with the latter solvent system was further fractionated using a Lobar Si-60 column with chloroform-methanol (25:1) and then purified by HPLC (silica gel, chloroform-methanol 30:1) to give manzamines E(31 mg) and F(111 mg).

Manzamine E

Colorless glass, $[\alpha]_D^{23}63.7°$ (C 2.51, CHCl$_3$); IR (CCl$_4$) 3540, 3360, 3125, 3075, 3000, 2920, 2860, 1735, 1655, 1480, 1450, 1400, 1375, 1350, 1300, 1260, 1180, 1145, 1095, 1065, 1050, 940, and 925 cm$^{-1}$; $^1$H NMR (CDCl$_3$) δ9.36 (1H, br s), 8.42 (1H, d, J=5.1 Hz), 8.10 (1H, d, J=7.9 Hz), 7.83 (1H, d, J=5.1 Hz), 7.59 (1H, d, J=7.9 Hz), 7.53 (1H, td, J=7.9, 1.1 Hz), 7.26 (1H, td, J=7.9, 1.1 Hz), 6.58 (1H, s), 5.64 (1H, dt, J=10.6, 7.8 Hz), 5.52 (1H, td, J=10.8, 4.6 Hz), 5.32 (br, s), 3.71 (1H, s), 3.36 (1H, td, J=12.2, 1.4 Hz), 3.23 (1H, dd, J=12.0, 6.7 Hz), 2.96 (2H, m), 2.77 (2H, m), and 2.64 −1.25 (complex); $^{13}$C NMR (CDCl$_3$) δ214.8s, 142.8s, 140.6s, 140.3s, 138.4d, 138.3d, 133.3s, 132.3d, 129.4s, 128.3d, 128.2d, 121.6s, 121.3d, 119.9d, 113.4d, 111.9d, 81.3d, 68.8t, 63.6d, 53.0t, 52.8t, 49.6t, 47.0t, 46.9s, 44.7t, 42.1d, 40.8t, 39.0t, 33.6t, 32.7t, 26.7t, 25.6t, 25.2t, 24.7t, and 21.5t. HRFABMS: Found m/z 565.3555 (M+H), Calcd for C$_{36}$H$_{45}$N$_4$O$_2$ 565.3543.

Manzamine F

Colorless crystals, mp 230° (dec), $[\alpha]_D^{23}+59.9°$ (c 1.67, CHCl$_3$); IR (KBr) 3250, 2995, 2920, 2860, 2780, 1685, 1580, 1555, 1440, 1410, 1365, 1340, 1260, 1215, 1105, 1065, 820, 785, 765, and 730 cm$^{-1}$; $^1$H NMR (CDCl$_3$) δ9.79 (1h, br s), 8.38 (1H, d, J=5.3 Hz), 7.80 (1H, d, J=5.3 Hz), 7.61 (1H, d, J=7.7 Hz), 7.14 (2H, m), 6.65 (1H, s), 5.63 (1H, dt, J=10.3, 7.9 Hz), 5.52 (1H, ddd, J=10.8, 10.8, 4.4 Hz), 3.68 (1H, s), 3.40 (1H, t, J=13.4 Hz), and 3.10-1.26 (complex); $^{13}$C NMR (CDCl$_3$) δ 216.2s, 143.1s, 142.8s, 141.3s, 138.2d, 137.3d, 133.6s, 133.1s, 132.5d, 130.1s, 128.0d, 123.2s, 121.1d, 113.8d, 113.4d, 112.4d, 81.7d, 69.0s, 69.0t, 63.6d, 53.0t, 52.8t, 49.6t, 47.3t, 46.5t, 45.1t, 42.3d, 39.9t, 38.8t, 34.0t, 32.7t, 26.6t, 25.5t, 25.0t, 24.4t, and 21.4t; EIMS m/z 578 (M-2H, 4), 562 (M-H$_2$O, 16), 544 (11), 424 (22), 273 (100), 178 (13), 138 (11), and 110 (20 rel.%). HRFABMS: m/z 581.3496 (M+H), calcd for C$_{36}$H$_{45}$N$_4$O$_3$ 581.3492.

EXAMPLE 4

Preparation of Reduced Derivative

Manzamine E and F are easily reduced to dihydro-, or tetrahydromanzamine E and F, respectively, by employing one, two, or three molar equivalents of hydrogen, respectively, in catalytic reduction. A sample of manzamine E or F and a small amount of catalyst such as Pd/C, Pt/C, or Raney Ni are mixed in a suitable solvent such as ethanol or methanol. The mixture is stirred in the presence of hydrogen in a hydrogenation apparatus. If the reaction is too slow, it can be facilitated by making the media slightly acidic by addition of a trace amount of acid such as HCl. When full reduction to prepare hexahydromanzamine E or F is desired, the reduction may be carried out under elevated pressure of hydrogen using an apparatus such as a Parr hydrogenation apparatus.

EXAMPLE 5

Preparation of Acid Salt

Since manzamines E and F are basic compounds, their acid salts are easily prepared by mixing manzamine B with an inorganic acid such as HCl, H$_2$SO$_4$, or an organic acid such as oxalic acid in aqueous ethanol or methanol.

ANTITUMOR ACTIVITIES OF THE COMPOUNDS OF THE INVENTION

The following assay method was utilized to illustrate the antitumor effectiveness of the compounds of Formula I corresponding to manzamines E and F of the examples.

P388 MOUSE LEUKEMIA CELL ASSAY

Maintenance of Cell Line

P388 mouse leukemia cells are grown in Dulbecco MEM medium with 10% horse serum, 4mM glutamine, and 20ug/ml gentamycin (Biologos, Inc.). Cells are incubated in 10% CO$_2$ and subcultured 2 times per week.

PROCEDURE

1. Add compound to each well of a 24-well plate or tube and allow solvent to evaporate to dryness.
2. Add 2ml (1.2×10$^5$) cells to each well or tube and mix.
3. Incubate in 10% CO$_2$, at 37° for 48 hours.
4. Read platees with an inverted microscope, scoring activity from 1+ to 4+ as follows: ND (not detectable), >90%; 1+, 75-90%; 2+, 50-74%; 3+, 25-49%; 4+, <25% of control growth. Cell counts are performed on each tube and results are reported as percent of control. Alternatively, scoring may be expressed as IC$_{50}$ which represents the minimum concentration of the composition required to inhibit 50% of the cell growth on the plate. Cell counts are performed on each tube and results are reported as percent of control.

The results of the above assay are summarized in Table 1.

TABLE 1

| Antitumor Assay Results of Manzamine B-D | |
| --- | --- |
| Composition | P388 IC$_{50}$ (µg/ml) |
| Manzamine E | 5.0 |
| F | 5.0 |

Table 1 shows that manzamines E and F have good antitumor activity at concentrations of at least 5 ug/ml against mouse leukemia cells.

It is apparent from the in vitro testing that the compositions of the invention, are effective for inhibiting or destroying tumor cells and tumors and therefore controlling diseases caused by or related to such tumors in hosts such as cancerous cachexia in fulfillment of the objects of the invention.

The scope of the present invention is not limited by the description, examples, and suggested uses herein and modifications can be made without departing from the spirit of the invention. For example, it may be noted that other derivatives of the compounds of examples 1 and 2 such as halogenated derivatives may possess antitumor activity analogous to those preferred embodiments described above. Further, the compositions described herein may have other useful applications such as, for example, analgesic applications.

Application of the compositions of the present invention can be accomplished by any suitable therapeutic method and technique as is presently or prospectively known to those skilled in the art. Therapeutic methods of the invention comprise the administration of antiviral effective amounts of one or more of the compounds of the invention as active ingredients, together with desired pharmaceutically acceptable diluents, adjuvants and carriers, to an animal suffering from a virus induced disease state. Unit dosage forms of compounds administrated according to the methods of the invention may be formulated by those skilled in the art to provide effective daily dosages that vary in accordance with body weight of the animal to be treated. Parenteral administration, and particularly intraperitoneal administration, are preferred routes for practice of the inventive methods. It is therefore intended that the present invention cover the modifications and variations of this invention provided that they come within the scope of the appended claims and their equivalents.

What is claimed is:

1. A substantially pure compound according to the formula:

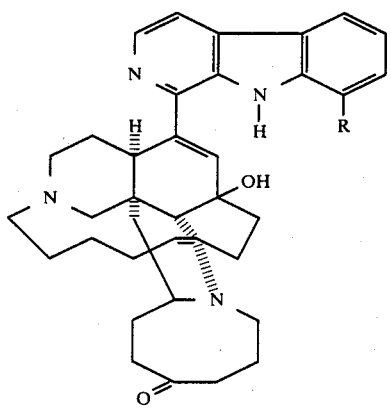

wherein
R is —H, —OH, —OCOA, or halogen and
A is Cl-C5 alkyl,
the dihydro and tetrahydro derivatives and mineral and organic acid salts thereof.

2. A compound of claim 1 wherein said mineral acid is selected from HCL, H$_2$SO$_4$, H$_3$PO$_4$ and HNO$_3$.

3. A substantially pure compound selected from the group consisting of:

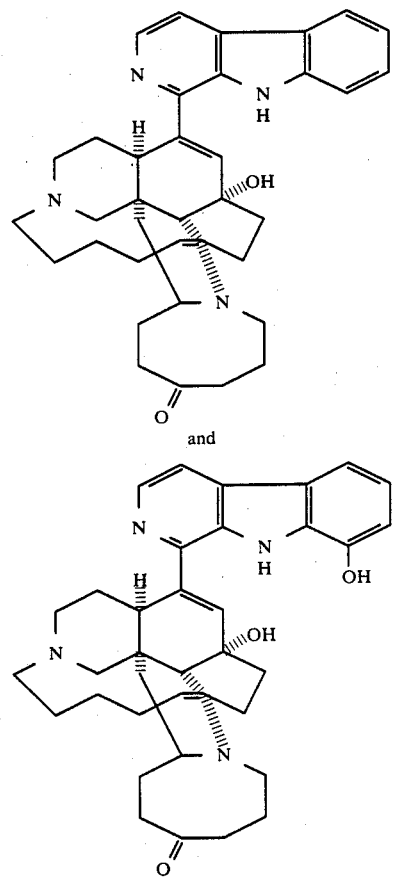

and

4. The dihydro and tetrahydro derivatives of a compound of claim 3.

5. A mineral or organic acid salt of a compound of claim 3.

6. A compound of claim 5 wherein said mineral acid is selected from HCL, H$_2$SO$_4$, H$_3$PO$_4$ and HNO$_3$.

7. A pharmaceutical composition comprising, as an active ingredient, an effective pharmaceutical amount of a compound of claim 1 and a non-toxic pharmaceutically acceptable carrier of diluent.

8. A pharmaceutical composition comprising, as an active ingredient, an effective pharmaceutical amount of a compound of claim 3 and a non-toxic pharmaceutically acceptable carrier of diluent.

* * * * *